(12) United States Patent
Deng et al.

(10) Patent No.: US 8,647,877 B2
(45) Date of Patent: Feb. 11, 2014

(54) PREPARATION AND USE OF NUCLEATED RED BLOOD CELL SIMULATING PARTICLES AND HEMATOLOGY CONTROL MIXTURES

(75) Inventors: Cheng Deng, Nanshan Shenzhen (CN); Zuyue Xu, Nanshan Shenzhen (CN); He Liu, Nanshan Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 389 days.

(21) Appl. No.: 12/975,053

(22) Filed: Dec. 21, 2010

(65) Prior Publication Data

US 2011/0159535 A1 Jun. 30, 2011

(30) Foreign Application Priority Data

Dec. 25, 2009 (CN) .......................... 2009 1 0215969

(51) Int. Cl.
*G01N 31/00* (2006.01)
*A01N 1/02* (2006.01)

(52) U.S. Cl.
USPC .............................................. 436/10; 435/2

(58) Field of Classification Search
None
See application file for complete search history.

(56) References Cited

U.S. PATENT DOCUMENTS

| | | | |
|---|---|---|---|
| 5,250,437 A * | 10/1993 | Toda et al. ..................... | 436/10 |
| 5,512,485 A | 4/1996 | Young et al. | |
| 5,858,790 A | 1/1999 | Kim et al. | |
| 6,187,590 B1 | 2/2001 | Kim et al. | |
| 6,200,500 B1 | 3/2001 | Ryan | |
| 6,221,668 B1 | 4/2001 | Ryan et al. | |
| 6,399,388 B1 | 6/2002 | Ryan et al. | |
| 6,403,377 B1 | 6/2002 | Ryan et al. | |
| 6,406,915 B2 | 6/2002 | Ryan et al. | |
| 6,448,085 B1 | 9/2002 | Wang et al. | |
| 6,653,137 B2 | 11/2003 | Ryan | |
| 6,723,563 B2 | 4/2004 | Ryan | |
| 6,911,313 B2 * | 6/2005 | Houwen et al. ................ | 435/7.2 |
| 6,962,817 B2 | 11/2005 | Li et al. | |
| 7,135,341 B2 | 11/2006 | Ortiz et al. | |
| 7,176,031 B2 | 2/2007 | Li et al. | |
| 7,195,919 B2 | 3/2007 | Jacobs et al. | |
| 7,198,953 B2 | 4/2007 | Ortiz et al. | |
| 7,285,417 B2 | 10/2007 | Ortiz et al. | |
| 7,354,767 B2 | 4/2008 | Ortiz et al. | |
| 7,754,487 B2 | 7/2010 | Ortiz et al. | |
| 2007/0072298 A1 | 3/2007 | Ortiz et al. | |
| 2010/0143955 A1 | 6/2010 | Baohua et al. | |

FOREIGN PATENT DOCUMENTS

| | | |
|---|---|---|
| CN | 1522298 | 8/2004 |
| EP | 0042969 | 5/1981 |
| EP | 0709458 | 10/1995 |
| JP | 2003009857 | 1/2003 |

OTHER PUBLICATIONS

Bunner et al., "Effects of Anthrax Toxin (Protective Antigen and Lethal Factor) on Human Monocytes and Polymorphonuclear Leukocytes", In Vitro Toxicology 6 (2) : 81-89 (1993).*
Burns et al., "Effect of Fixation with Formalin on Flow Cytometric Mearsurement of DNA in Nucleated Blood Cells", Aquaculture 55 : 149-155 (1986).*
Chinese Master's Dissertation with English Abstract, Jun. 8, 2011.
Chinese Search Report with English Summary dated Mar. 17, 2010.

* cited by examiner

*Primary Examiner* — Sandra Saucier
(74) *Attorney, Agent, or Firm* — Kory D. Christensen; Matthew S. Bethards; Stoel Rives LLC

(57) ABSTRACT

The present disclosure provides a nucleated red blood cell simulating particle, which may be leukocytes bound to a fluorescent-staining inhibitor capable of stably binding to the nucleus or a nucleic acid in a cell so as to reduce the binding capacity of the particles to a fluorescent dye during their detection. The present disclosure also provides a method for preparing nucleated red blood cell simulating particles, including the following steps: (a) obtaining purified leukocytes; (b) suspending the leukocytes in a cell treatment solution containing a fluorescent-staining inhibitor which stably binds to the nucleus or a nucleic acid in a cell, and (c) washing the obtained product. The present disclosure also provides a hematology control mixture containing the nucleated red blood cell simulating particles. In addition, the present disclosure describes the use of the nucleated red blood cell simulating particles and the hematology control mixtures comprising the same, for the quality control of a blood cell analyzer.

18 Claims, 5 Drawing Sheets

PREPARATION AND USE OF NUCLEATED RED BLOOD CELL SIMULATING PARTICLES AND HEMATOLOGY CONTROL MIXTURES

RELATED APPLICATIONS

This application claims priority to Chinese Patent Application No. 200910215969.X, filed Dec. 25, 2009, the disclosure of which is fully incorporated herein by reference.

TECHNICAL FIELD

The present disclosure relates to hematology control mixtures for blood analysis quality control. In particular, the present disclosure relates to nucleated red blood cell simulating particles, hematology control mixtures including the nucleated red blood cell simulating particles, and preparation methods thereof, as well as use of the nucleated red blood cell simulating particles and the hematology control mixtures for the quality control of a blood cell analyzer which detects via fluorescent-scattered light methods.

DETAILED DESCRIPTION

Figure 1:
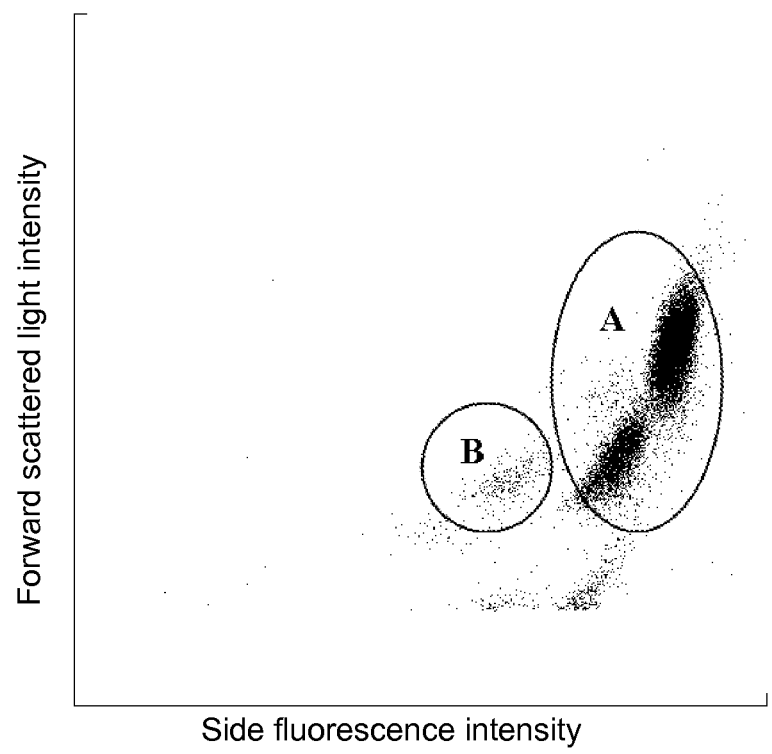
FIG. 1 is a scatter diagram of a clinical blood sample containing the nucleated red blood cells (only the channel of the nucleated red blood cells is provided), in which the abscissa axis represents the side fluorescence intensity, and the longitudinal axis represents the forward scattered light intensity.

Normal mature human red blood cells do not contain nuclei. In some instances, including certain pathological conditions, nucleated red blood cells (NRBCs), i.e. erythroblasts, which are immature erythrocytes, will appear in human peripheral blood. The detection of the nucleated red blood cells may provide diagnostic information for certain diseases. Various advanced blood cell analyzers are equipped with a function for detecting the nucleated red blood cells, using impedance and/or fluorescent-scattered light methods.

For quality control of a blood cell analyzer equipped with the ability to detect nucleated red blood cells, it is necessary to use hematology control mixtures including nucleated red blood cell simulating particles. There are previous reports of preparing nucleated red blood cell simulating particles.

U.S. Pat. Nos. 7,176,031 and 6,962,817 disclose a method for simulating human nucleated red blood cells with an artificially synthesized particle. The disadvantages of the method are the complicated production process and the relatively high cost of the synthetic particles. U.S. Pat. No. 7,354,767 discloses a method for preparing nucleated red blood cell simulating particles using common mammalian red blood cells (without nuclei). The simulating particles prepared by this method are similar in size to the nuclei of human nucleated red blood cells, and are suitable for use with a blood cell analyzer that detects nucleated red blood cells using an impedance method. However, such particles do not contain a cell nucleus and thus are not suitable for simulating the fluorescent properties of human nucleated red blood cells stained with a fluorescent dye. U.S. Pat. No. 7,195,919 discloses a method for simulating the fluorescent properties of human nucleated red blood cells by linking a biological macromolecule (e.g. a nucleic acid or a peptide chain) on to the surface of the red blood cells. The shortcomings of this method include the complicated process and the high cost of the biological macromolecule as a raw material.

U.S. Pat. Nos. 6,723,563 and 6,653,137 disclose preparing nucleated red blood cell simulating particles using the blood cells from birds (e.g. turkey or chicken), reptiles (e.g. alligator), or fish (e.g. salmon) as a raw material. U.S. Pat. Nos. 6,406,915, 6,403,377, 6,399,388, 6,221,668 and 6,200,500 disclose methods for preparing nucleated red blood cell simulating particles using turkey red blood cells. U.S. Pat. No. 6,448,085 discloses a method for preparing nucleated red blood cell simulating particles using chicken erythrocytes. U.S. Pat. Nos. 6,187,590 and 5,858,790 disclose methods for preparing nucleated red blood cell simulating particles using red blood cells from turkey, chicken and salmon. U.S. Pat. Nos. 7,285,417, 7,135,341 and 7,198,953 disclose methods for preparing nucleated red blood cell simulating particles using alligator red blood cells. A common feature of these methods lies in that the animal red blood cells containing nuclei including red blood cells from birds, reptiles and fish are used to simulate the human nucleated red blood cells. However, the red blood cells of most of the birds, reptiles and fish are oval in shape, which is different from human nucleated red blood cells, which are generally more round in morphology. Thus, in some cases, such animal nucleated erythrocytes cannot simulate human nucleated red blood cells well. For example, when using flow cytometry to detect cells, the orientation of the oval cells passing through the flow chamber is inconsistent, thereby resulting in forward scattered light signals which exhibit differences in their magnitude, whereas more rounded cells will not exhibit this phenomenon.

The present disclosure provides simple, cost-effective methods to obtain nucleated red blood cell simulating particles with better simulatory effects, especially for the nucleated red blood cell simulating particles that are suitable for the quality control of blood cell analyzers employing fluorescent-scattered light methods for detection.

In an embodiment, the present application discloses a nucleated red blood cell simulating particle, which may be a leukocyte or leukocyte subpopulation bound to a fluorescent staining inhibitor capable of stably binding to the nucleus or a nucleic acid in a cell, so as to reduce the binding capacity of the particle to the fluorescent dyes during detection.

The fluorescent-staining inhibitor may be selected from at least one of the following: a non-fluorescent dye, a fluorescent dye with a fluorescence quantum yield lower than that of the fluorescent dye used for detection, a fluorescent dye which has a fluorescence spectrum significantly different from the fluorescent dye used for detection, and a compound capable of binding to a nucleoside.

In another embodiment, the present disclosure provides a hematology control mixture including the nucleated red blood cell simulating particles according to the present disclosure.

In still another embodiment, the present disclosure provides a method for preparing a nucleated red blood cell simulating particle, comprising: enriching leukocytes or a leukocyte subpopulation in blood containing leukocytes; suspending the obtained leukocytes or leukocyte subpopulation in a cell treatment solution containing a fluorescent staining inhibitor capable of stably binding to the nucleus and nucleic acid in a cell; and washing the obtained product.

In still another embodiment, the present disclosure provides a method for preparing a hematology control mixture, by mixing the nucleated red blood cell simulating particles according to the present disclosure with one or more other blood cell simulating agents such as leukocytes, erythrocytes and platelets in a cell storage solution.

In still another embodiment, the present disclosure relates to the use of the nucleated red blood cell simulating particles and the hematology control mixture for the quality control of a blood cell analyzer.

The present disclosure also relates to the use of a fluorescent staining inhibitor in the preparation of the nucleated red blood cell simulating particles.

In the methods of the present disclosure, the leukocytes or a leukocyte subpopulation are treated with a fluorescent-staining inhibitor to more closely simulate the human nucleated red blood cell without using nucleic acids or similar biological polymers. The procedure is simple, the cost is low, and the industrial production of the hematology control mixture is efficient. Other aspects of the present disclosure will be apparent with reference to the following description and embodiments.

Nucleated Red Blood Cell Simulating Particles.

In an embodiment, a nucleated red blood cell simulating particle is provided. The nucleated red blood cell simulating particle is a leukocyte or a leukocyte subpopulation bound to a fluorescent-staining inhibitor which binds to the nucleus or a nucleic acid in a cell so as to reduce the binding capacity of the particle to the fluorescent dye used for detection, wherein the fluorescent-staining inhibitor is selected from a non-fluorescent dye, a fluorescent dye which has a fluorescence quantum yield lower than that of the fluorescent dye used for detection, a fluorescent dye whose fluorescence spectrum is significantly different from that of the fluorescent dye used for detection, and a compound capable of binding to a nucleoside. The nucleated red blood cell simulating particle is suitable for use in a hematology analyzer which detects nucleated red blood cells by fluorescent-scattered light methods.

In general, a fluorescent-scattered light method for detecting nucleated red blood cells includes the steps of: treating a blood sample with a hemolytic agent and a fluorescent dye used for detection in order to lyse the red blood cells while the leukocytes and the nucleated red blood cells bind to and are stained by the fluorescent dye used for detection. The stained cells are detected by flow cytometry and the nucleated red blood cells and leukocytes can be differentiated based on the fluorescence intensity and the scattered light intensity signals, and thereby the nucleated red blood cells can be counted. For example, Chinese patent application No. 200810218267.2 discloses a method for detecting nucleated red blood cells, including the steps of: treating blood with a hemolytic agent and a fluorescent dye used for detection to lyse the red blood cells while the leukocytes and the nucleated red blood cells bind to the fluorescent dye used for detection. The stained cells are detected by flow cytometry, and the side fluorescence (SFL) and the forward scattered light (FSC) intensity signals are collected. Due to fewer nucleic acids in the nucleated red blood cells than the leukocytes, the intensity of the nucleated red blood cells is less than that of leukocytes when both kinds of cells are detected by fluorescent-scattered light methods.

In the SFL-FSC scatter diagram of a clinical blood sample containing nucleated red blood cells detected by a fluorescent-scattered light method, the areas of leukocytes and nucleated red blood cells are indicated in FIG. 1, in which A is the area of leukocytes and B is the area of nucleated red blood cells. From FIG. 1, it appears that the fluorescence intensity of the nucleated red blood cells is lower than that of the leukocytes, while the scattered light characteristics of certain leukocyte subpopulations is similar to that of the nucleated red blood cells.

The nucleated red blood cell simulating particles in an embodiment of the present disclosure may be leukocytes or a leukocyte subpopulation bound to a fluorescent-staining inhibitor, wherein the inhibitor binds to the nucleus or a nucleic acid in the cell and wherein the dissociation of the inhibitor is low in an aqueous solution (i.e. the inhibitor is stably bound). The inhibitor occupies a portion of the sites which may be bound by the fluorescent dye used for detection, and thus inhibits to some extent the binding of the fluorescent dye to the leukocyte, i.e. reducing the binding capacity of leukocytes to the fluorescent dye. This results in the decrease of the fluorescent intensity of leukocytes, so as to simulate the fluorescent properties of nucleated red blood cells.

According to the present disclosure, the fluorescent staining inhibitor refers to a substance which stably binds to a nucleus or a nucleic acid, pre-occupies or protects a site at which a cell is bound by a fluorescent dye used for detection, and inhibits the binding of the fluorescent dye used for detection to the nucleus or the nucleic acid. In the fluorescent detection, the treated leukocytes or leukocyte subpopulation form a cell population in the scatter diagram, which is in the same area as nucleated red blood cells. If nucleated red blood cell simulating particles are added to leukocytes in a certain ratio, then detected by a hematology analyzer employing the fluorescent-light scattering detection, there will be two distinct cell populations within the limits of detection in the scatter diagram, one in the area of leukocytes and the other in the area of nucleated red blood cells, so as to achieve proper quality control for the counting of nucleated red blood cells.
Methods for Preparing Nucleated Red Blood Cell Simulating Particles.

In an embodiment of the present disclosure, a method for preparing a nucleated red blood cell simulating particle is provided, comprising the steps of: washing and isolating the anti-coagulant treated blood to obtain purified leukocytes, or further purifying the leukocytes to obtain a leukocyte subpopulation, such as granulocytes or lymphocytes; suspending the leukocytes or leukocyte subpopulation in a cell treatment solution containing a fluorescent-staining inhibitor, in which the nucleus or nucleic acid of a cell stably binds to the inhibitor; and washing the obtained product.

The fluorescent-staining inhibitor is selected from at least one of the following: a non-fluorescent dye, a fluorescent dye which has a fluorescence quantum yield lower than that of the fluorescent dye used for detection, a fluorescent dye whose fluorescence spectrum is significantly different from that of the fluorescent dye used for detection, and a compound capable of binding to a nucleoside.

Many methods for obtaining leukocytes are available, e.g. the routine washing and purification methods of leukocytes. In an embodiment of the present disclosure, the red blood cells are removed from the blood by lysis with or without precipitation, and the purified leukocytes are obtained after centrifugation or after standing, etc. These obtained leukocytes can be further purified by a common method in order to obtain a leukocyte subpopulation, such as granulocytes or lymphocytes. A commercial cell isolation solution can also be used, and the purified cells can be obtained according to the instructions of the manufacturer.

The blood used in the present disclosure can be any blood sample containing human or animal leukocytes, such as fish, amphibians, reptiles, birds or mammals. For example, the blood of a mammal such as a mouse, rat, pig, sheep, cattle or human is used. In an embodiment of the present disclosure, the whole blood containing leukocytes or a blood cell mixture containing leukocytes, such as a mixture of leukocytes and erythrocytes, can be directly treated, or the purified leukocytes or a leukocyte subpopulation such as granulocytes or lymphocytes can be treated, by the method disclosed.

The obtained cells may be suspended in a cell treatment solution containing a fluorescent-staining inhibitor and incubated for a period of time sufficient to make the inhibitor stably bind to the nucleus or nucleic acid in the cells.

In an embodiment of the present disclosure, one or more fluorescent-staining inhibitors are used to treat leukocytes or a leukocyte subpopulation so as to reduce the binding capacity of the cells to the fluorescent dye used for detection. In this way, after staining by the fluorescent dye used for detection, the fluorescence intensity of the treated leukocytes or leukocyte subpopulation is lower than that of the untreated leukocytes, so as to simulate the fluorescence properties of nucleated red blood cells. In another embodiment, the scattered light characteristics of the leukocytes or leukocyte subpopulation is similar to that of the nucleated red blood cells. The binding of the fluorescent-staining inhibitor to the nucleus or nucleic acid in the cell does not affect the particle in the cell, the size and the morphology of the cell, and thus the scattered light characteristics of the cell are retained. The treated cells simulate the fluorescence properties and scattered light characteristics of the nucleated red blood cells, and can be used as nucleated red blood cell simulating particles in a hematology control.

Below, an embodiment of the present disclosure is illustrated by an example of a nucleic acid fluorescent dye widely used for hematology analyzers.

Nucleic acid fluorescent dyes bind to nucleic acid components, including DNA and RNA, in a cell to make the cell emit fluorescence upon laser excitation. For such fluorescent dyes, a fluorescent-staining inhibitor with the following properties can be selected to lower the fluorescence of leukocytes: capable of binding to a nucleic acid or another component in the nucleus, such as a protein; pre-occupying a binding site for the fluorescent dye used for detection; or occupying a site adjacent to the binding site. This will generate steric hindrance so as to prevent the fluorescent dye used for detection from entering the binding site, thereby inhibiting to some extent the binding of the fluorescent dye used for detection of the nucleic acid. Skilled persons in the art would understand that several compounds could be used as the fluorescent staining inhibitor, which may have the following two properties:

1. It is capable of binding to the nucleus or a nucleic acid in a cell, and then preventing to some extent the binding of the cell to the fluorescent dye used for detection in the hematology analyzer;

2. After the compound binds to the cell, it itself does not emit fluorescence or its fluorescence intensity is weak, or although emitting fluorescence, its fluorescence spectrum differs significantly from that of the fluorescent dye used in the hematology analyzer, and thus its fluorescence signal is not excited or detected by the instrument.

Such a fluorescent staining inhibitor may be a non-fluorescent dye which stains the nucleus, including, for example, a single-component dye such as Methylene Blue, Toluidine Blue O, Trypan Blue, Safranine T or hematoxylin, and a mixed type dye including multiple components such as Wright's stain or Giemsa stain.

Such a fluorescent-staining inhibitor may alternatively be a fluorescent dye, including:

(1) A fluorescent dye which stains the nucleus or a nucleic acid, provided that its fluorescence quantum yield is lower than that of the fluorescent dye used for detection, thus not interfering with the detected fluorescence signals, such as Neutral Red. Neutral Red is a fluorescent dye. Upon binding to a nucleic acid, under certain conditions, its fluorescence is quenched and its fluorescence quantum yield is low. Neutral Red may be used as fluorescent-staining inhibitor to prepare a nucleated red blood cell simulating particle, in a concentration of Neutral Red similar to that for routine cell staining.

(2) A fluorescent dye which stains the nucleus or a nucleic acid, provided that its fluorescence spectrum differs from that of the fluorescent dye used for detection in the hematology analyzer sufficiently to enable its fluorescence signal to not be excited by or detected by the instrument. For example, red light of 630 nm wavelength may be used as the excitation light in a hematology analyzer. The wavelengths of the excitation light and emitting light of a fluorescent detection dye may be 630 nm and 660 nm, respectively. Fluorescent dyes which may be used as the inhibitor dye in this example include, but are not limited to, Acridine Orange (excitation wavelength 488 nm, emitting wavelength 515 nm), Hoechst 33342 (excitation wavelength 350 nm, emitting wavelength 461 nm), YO-PRO-1 (excitation wavelength 491 nm, emitting wavelength 509 nm) and Propidium Iodide (excitation wavelength 530 nm, emitting wavelength 625 nm).

Such a fluorescent-staining inhibitor may also be a compound capable of binding to a nucleoside, such as Dactinomycin D. Dactinomycin D inserts into the double stands of DNA and binds to guanine groups. It can stably bind to a nucleic acid and occupy a binding site for the fluorescent dye used for detection, thereby to some extent inhibiting the binding of the fluorescent dye to the nucleic acid during detection.

The cells may be suspended in solution and the dye mentioned above (which may be pre-dissolved in a suitable solvent to prepare a stock solution) may be added to stain the cells. Alternatively, a cell treatment solution may be prepared by dissolving the dye in a suitable solvent and then the cells are suspended in the cell treatment solution for staining. The dye stock solution can be formulated according to the routine formulation of the solutions. The staining time varies with the specific dye and its concentration, but is usually in a range from between 15 minutes to 1 hour. The concentration of the dye varies with the type, and a typical concentration of the dye for staining is appropriate, e.g. 0.01 to 1 g/l of Toluidine Blue O, 0.2 to 2 g/l of Wright's stain and 0.1 to 10 g/l of Neutral Red. Skilled persons in the art would understand that the staining time is related to the concentration of the solution and the temperature. In the case that a higher concentration is used, the staining time is shorter, and the higher the temperature, the shorter the staining time. The degree of the staining is affected by factors such as the type of the dye, concentration, staining temperature and staining time, and these factors may be interrelated. In an embodiment of the disclosure, leukocytes or a leukocyte subpopulation are partially stained to retain part of the binding capacity of the cells to the fluorescent dye used for detection. With the aid of a hematology analyzer that detects via fluorescent-scattered light methods, the appropriate staining concentration, staining temperature and staining time for a dye may be determined so as to make the treated cells to appear in the area of nucleated red blood cells shown in the SFL-FSC scattered diagram.

After staining the cells, the surplus dye may be removed by washing the cells. A neutral isoosmotic buffer commonly used by skilled persons in the art can be used as a washing solution in the embodiment of the present disclosure. For example, the washing solution may include a neutral isoosmotic phosphate buffer, a neutral isoosmotic borate buffer, a neutral isoosmotic citrate buffer and saline. Generally, the cells are centrifuged or allowed to stand to remove the supernatant, and then resuspended in the washing solution. This may be repeated several times to remove the excess dye.

In an embodiment, a suitable fixative is added to the washed cells to fix the cell membrane of the stained cells so as to increase the stability. The fixation can be performed according to a known method to skilled persons in the art. Suitable cell fixatives include alcohols, aldehydes, mercury salts, osmic acid, and potassium dichromate. The cell washing may alternatively be carried out after fixation, instead of after staining.

In an embodiment of the present disclosure, the prepared nucleated red blood cell simulating particle is stored in a cell storage solution. Common cell storage solutions known to the skilled persons in the art are suitable. If the prepared nucleated red blood cell simulating particles are suspended in a cell storage solution, it may be convenient for injecting the particles into a hematology analyzer.

Hematology Control Mixture.

In an embodiment of the present disclosure, a hematology control mixture incorporating the disclosed nucleated red blood cell simulating particles is provided. The nucleated red blood cell simulating particles prepared by the disclosed methods can be mixed with another cell simulating agent such as a red blood cell, leukocyte and platelet to form a hematology control mixture for use with a multi-parameter hematology analyzer which can detect fluorescence stains, in which the ratio of the nucleated red blood cells to leukocytes can be adjusted as needed.

In an embodiment of the present disclosure, the use of the nucleated red blood cell simulating particles and the hematology control mixture in the quality control of a hematology analyzer is provided. In an embodiment of the present disclosure, the nucleated red blood cell simulating particles may be quantitatively suspended in a cell suspension to prepare a nucleated red blood cell simulating particle suspension with a known concentration, which in turn may be injected into a hematology analyzer. Alternatively, the hematology control mixture of the present disclosure may be injected into a hematology analyzer. The analyzer will detect the scattered light and fluorescence signals, report the results of the classification and count of nucleated red blood cells, and compare it to the known concentration.

In yet another embodiment of the present disclosure, the use of the fluorescent-staining inhibitor in the preparation of nucleated red blood cell simulating particles is provided. In a further embodiment, a method of using a hematology control mixture for the detection of nucleated red blood cells is provided.

EXAMPLES

The present disclosure will be further described with reference to the following Examples. The Examples are intended only to be illustrative, but not to limit the scope of the present disclosure in any sense.

Unless otherwise indicated, the hematology detection device used in the following examples is a BC series flow cytometer with a detection wavelength of 640 nm produced by SHENZHEN MINDRAY BIO-MEDICAL ELECTRONICS CO., LTD. The detection method and reagent formulations are that of Example 1 of US Publication No. 2010-0143955A1, which is incorporated herein by reference.

Unless otherwise indicated, the reagents used in the examples are all A.R. grade.

The reagents used in the examples include:

PBS, formed by mixing 0.4 g of $NaH_2PO_4.2H_2O$, 2.2 g of $Na_2HPO_4.12H_2O$ and 8.5 g of NaCl and dissolving them in distilled water to a final volume of 1 L.

Lymphocyte isolation kit purchased from TIAN JIN HAO YANG BIOLOGICAL MANUFACTURE CO., LTD.

Toluidine Blue O staining solution, formed by dissolving 1 g of Toluidine Blue O dye in 100 ml of 70% ethanol.

Wright's staining solution, formed by dissolving 0.1 g of Wright's stain in 60 ml of methanol.

Neutral Red staining solution, formed by dissolving 1 g of Neutral Red dye in 1 L of PBS.

Acridine Orange staining solution, formed by preparing a stock solution of 5 mg/ml by dissolving Acridine Orange in PBS, and used in a ratio of 1%.

Example 1

A fresh bovine anti-coagulated blood sample was obtained and treated with 0.9% $NH_4Cl$ solution to lyse the red blood cells. Bovine leukocytes were isolated by centrifugation at 3000 rpm and the supernatant containing erythrocyte debris and hemoglobin was discarded. The precipitated leukocytes were suspended in PBS and adjusted to a cell density of about $1 \times 10^{10}$ cells/liter. One ml of Toluidine Blue O staining solution was added into 10 ml of the leukocyte suspension and mixed thoroughly. Staining was performed at 30° C. for 30 minutes. The stained leukocytes were isolated by centrifugation at 3000 rpm, washed and then re-suspended in PBS.

Aliquots of the stained leukocyte suspension and of an unstained leukocyte suspension for a control were adjusted to a cell density of $10^{10}$ cells/liter and fixed by the addition of formaldehyde. The fixed cells were isolated by centrifugation at 3000 rpm, washed and then re-suspended in PBS. The fixed cells were detected using the reagents and method as described in Example 1 of US Publication No. 2010-0143955A1 to obtain a SFL-FSC scatter diagram (Channel NRBC).

Figure 2:
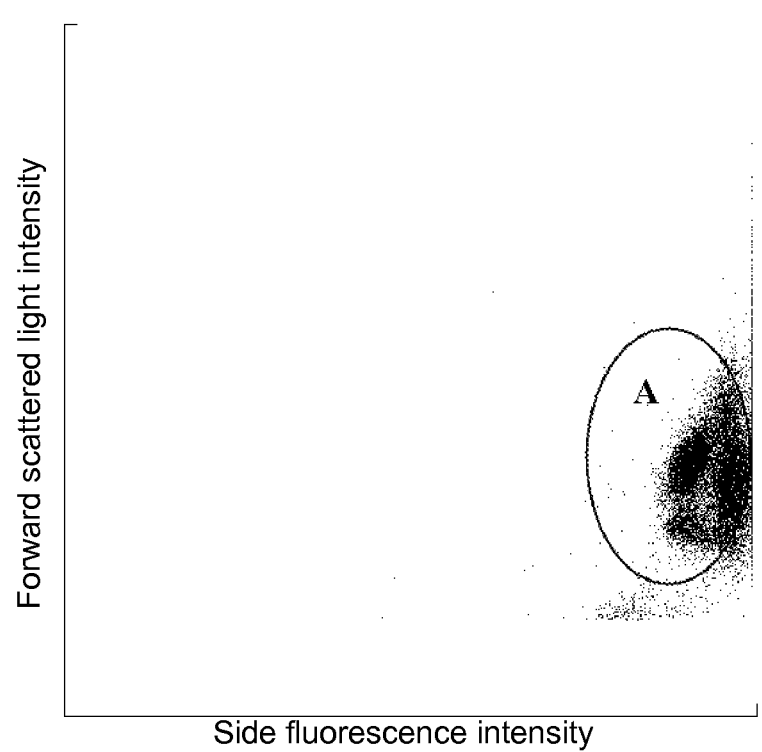
FIG. 2 is a scatter diagram of the unstained leukocytes in Example 1 (only the channel of the nucleated red blood cells is provided), in which A is the area of leukocytes. The abscissa axis represents the side fluorescence intensity, and the longitudinal axis represents the forward scattered light intensity.

The scatter diagram of the unstained leukocytes is shown in FIG. 2, in which area A is of leukocytes.

Figure 3:
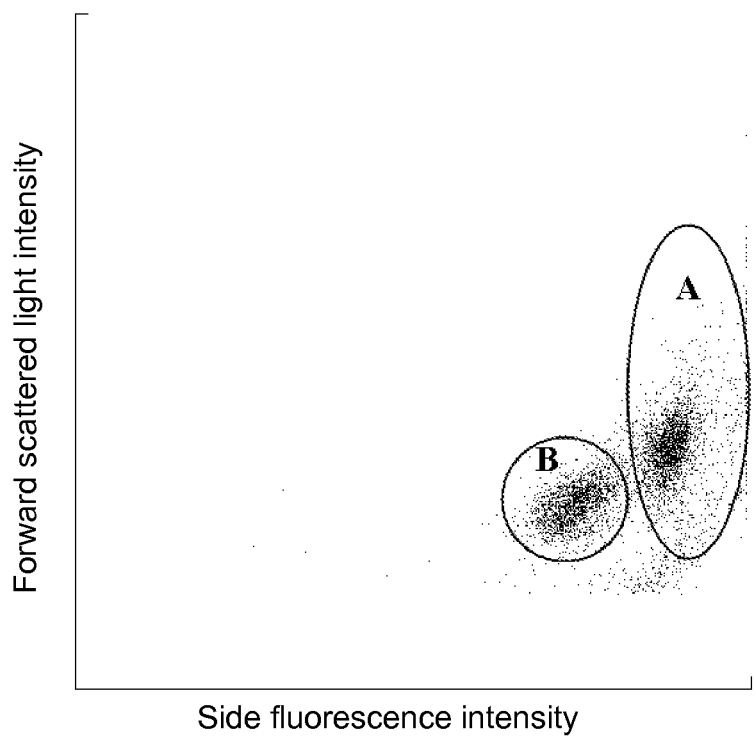
FIG. 3 is a scatter diagram of the leukocytes stained with Toluidine Blue O in Example 1 (only the channel of the nucleated red blood cells is provided), in which A is the area of leukocytes and B is the area of the nucleated red blood cells. The abscissa axis represents the side fluorescence intensity, and the longitudinal axis represents the forward scattered light intensity.

The scatter diagram of the leukocytes stained with Toluidine Blue O is shown in FIG. 3. After staining by Toluidine Blue O, the fluorescence intensity of leukocytes in FIG. 3 is decreased compared to that of FIG. 2. The decrease in the intensity of different subpopulations of leukocytes is different, and two groups are indicated in the figure. Area A still exhibits the characteristics of leukocytes, and area B is capable of simulating nucleated red blood cells.

The leukocytes used in Example 1 include granulocytes, lymphocytes and monocytes, so two groups appear in the SFL-FSC scatter diagram after staining. In this way, it is possible to directly simulate both leukocytes and nucleated red blood cells without adding other components to the hematology control mixture. However, if a whole blood hematology control mixture is to be prepared by mixing nucleated red blood cell simulating particles with other cell simulating particles, the cells of area A in FIG. 3 may interfere with the counting of other channels, e.g. the classification of leukocytes. Therefore, in an embodiment, purified nucleated red blood cell simulating particles may be prepared. In Examples 2 and 3, this was achieved by isolating and purifying the leukocytes.

Example 2

A fresh porcine anti-coagulated blood sample was obtained and settled for a period of time to allow red blood cells to separate. The supernatant, rich with leukocytes, was pipetted and centrifuged at 3000 rpm to separate leukocytes, and the supernatant was discarded. The precipitated red blood cells and leukocytes were re-suspended in 0.9% $NH_4Cl$ solution to lyse red blood cells. The porcine leukocytes were isolated at 3000 rpm, the supernatant including erythrocyte debris and hemoglobin, etc., was discarded, and the precipitated leukocytes were re-suspended in PBS. Following the instructions of the manufacturer, porcine granulocytes were isolated using the lymphocyte isolation kit and then washed with PBS. The porcine granulocyte suspension was centrifuged at 1200 rpm, the supernatant was discarded, and the porcine granulocytes were harvested. Ten ml of Wright's staining solution was added into the porcine granulocytes and pipetted to suspend the porcine granulocytes. Immediately, an equal volume of PBS to Wright's staining solution was added and mixed homogeneously to a cell density of $2\sim3\times10^{10}$ cells/liter. The staining was performed at 30° C. for 30 minutes. The stained leukocytes were isolated by centrifuging at 1200 rpm, washed and re-suspended in PBS.

Aliquots of the stained porcine granulocyte suspension, and of an unstained porcine granulocyte suspension as a control, were adjusted to a cell density of $2\sim3\times10^{10}$ cells/liter and fixed by the addition of 1% formaldehyde. The fixed granulocytes were isolated by centrifugation at 1200 rpm, washed and then re-suspended in PBS. The fixed cells were detected using the reagents and methods as described in Example 1 to obtain a SFL-FSC scatter diagram.

Figure 4:
FIG. 4 is a scatter diagram of the unstained granulocytes in Example 2 (only the channel of the nucleated red blood cells is provided). The abscissa axis represents the side fluorescence intensity, and the longitudinal axis represents the forward scattered light intensity.

The scatter diagram of the unstained porcine granulocytes is shown in FIG. 4, in which area A is of granulocytes.

Figure 5:
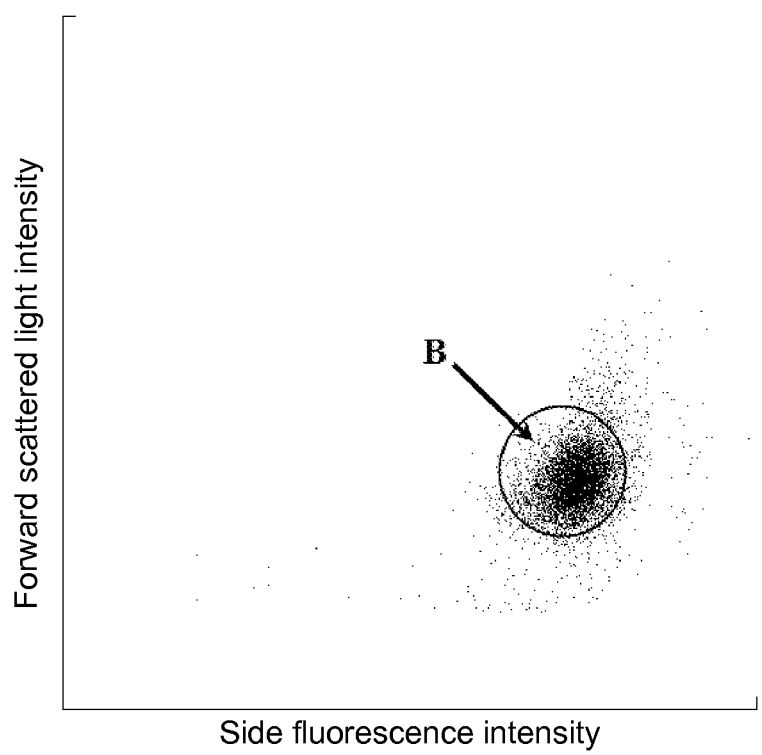
FIG. 5 is a scatter diagram of the granulocytes stained with Wright's stain in Example 2 (only the channel of the nucleated red blood cells is provided). The abscissa axis represents the side fluorescence intensity, and the longitudinal axis represents the forward scattered light intensity.

The scatter diagram of the porcine granulocytes stained with Wright's stain is shown in FIG. 5. After staining with Wright's stain, compared to FIG. 4, the fluorescence intensity of granulocytes in FIG. 5 appears to be decreased and the degree of decrease is homogeneous. The treated granulocytes fall into area B and are capable of simulating nucleated red blood cells. The porcine granulocytes were formulated to provide a cell suspension which has a sufficient density to be used as nucleated red blood cell simulating particles, and may be conveniently mixed with other hematology control mixture components such as leukocytes, erythrocytes, and platelets for preparing whole blood hematology control mixtures.

Figure 6:
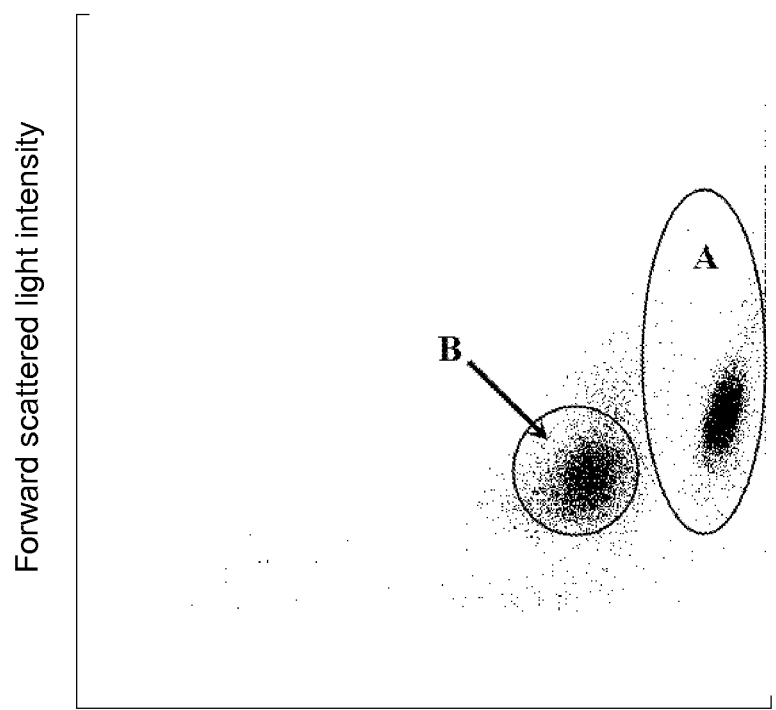
FIG. 6 is a scatter diagram of the mixture of the unstained granulocytes and the granulocytes stained with Wright's stain in Example 2 (only the channel of the nucleated red blood cells is provided). The abscissa axis represents the side fluorescence intensity, and the longitudinal axis represents the forward scattered light intensity.

The scatter diagram of the mixture of the unstained porcine granulocytes and the porcine granulocytes stained with Wright's stain is shown in FIG. 6, in which area A is of granulocytes and area B is of nucleated red blood cells.

Example 3

Fresh bovine anti-coagulated blood was taken and treated with 0.9% $NH_4Cl$ solution to lyse the red blood cells. Bovine leukocytes were isolated by centrifugation at 3000 rpm and the supernatant containing erythrocyte debris and hemoglobin was discarded. The precipitated leukocytes were suspended in PBS. Following the instructions of the manufacturer, bovine granulocytes were isolated by the lymphocyte isolation kit and then washed with PBS. The bovine granulocyte suspension was centrifuged at 1200 rpm, the supernatant was discarded, and the bovine granulocytes were harvested. The bovine granulocytes were suspended in Neutral Red staining solution, adjusted to a cell density of about $2\sim3\times10^{10}$ cells/liter, and fixed by the addition of 1% formaldehyde. As a control, an aliquot of the bovine granulocytes was directly fixed in PBS containing 1% formaldehyde but not containing the dye. The fixed cells were isolated by centrifugation at 1200 rpm, washed and then re-suspended in PBS. The fixed cells were detected using the reagents and method as described in above Example 1 to obtain a SFL-FSC scatter diagram.

Figure 7:
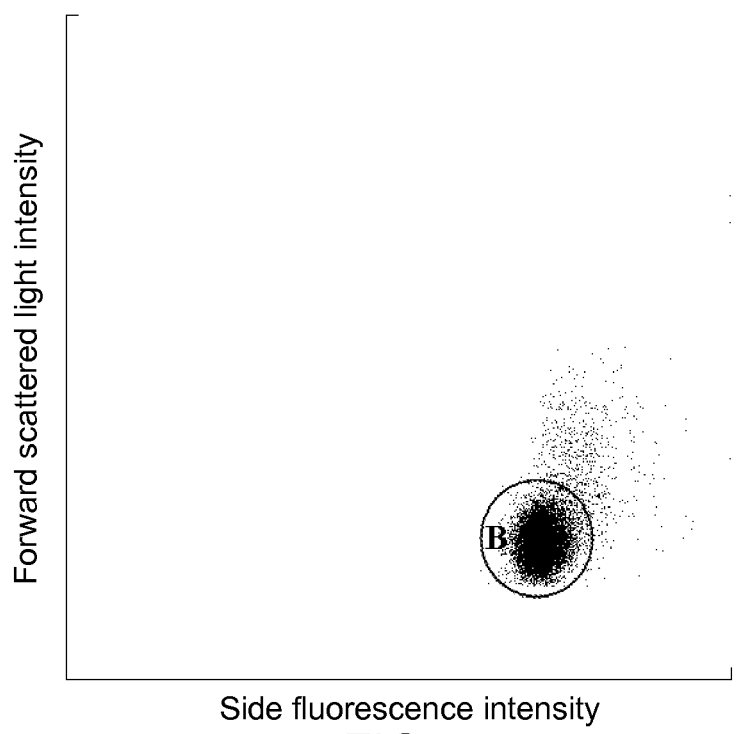
FIG. 7 is a scatter diagram of the granulocytes stained with Neutral Red in Example 3 (only the channel of the nucleated red blood cells is provided). The abscissa axis represents the side fluorescence intensity, and the longitudinal axis represents the forward scattered light intensity.
Figure 8:
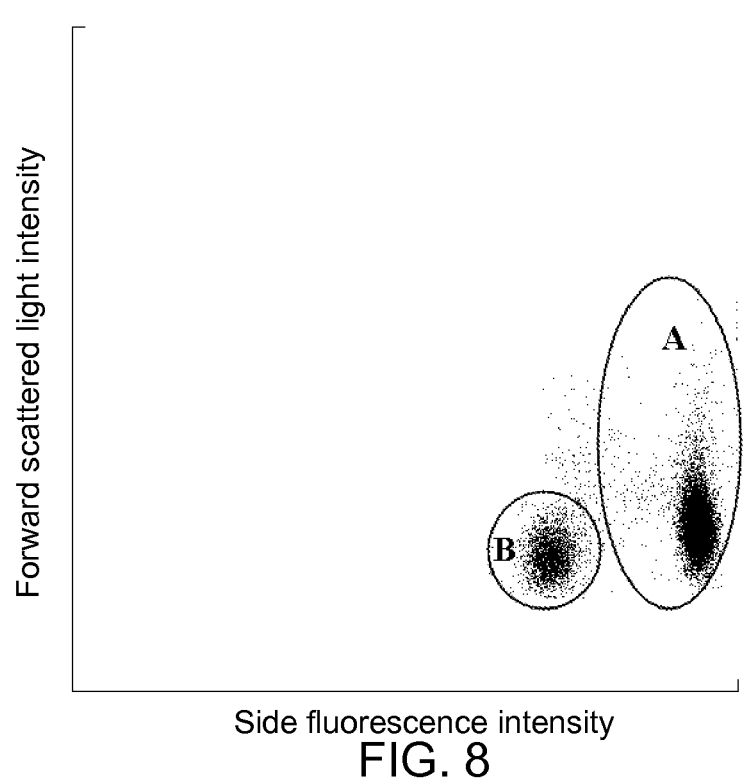
FIG. 8 is a scatter diagram of the mixture of the unstained granulocytes and the granulocytes stained with Neutral Red in Example 3 (only the channel of the nucleated red blood cells is provided). The abscissa axis represents the side fluorescence intensity, and the longitudinal axis represents the forward scattered light intensity.

The scatter diagram of the bovine granulocytes stained with Neutral Red is shown in FIG. 7. The scatter diagram of the mixture of the unstained bovine granulocytes and the bovine granulocytes stained with Neutral Red is shown in FIG. 8. In FIGS. 7 and 8, area A is of granulocytes and area B is of nucleated red blood cells.

Example 4

Following the method of Example 3, bovine granulocytes were prepared, suspended in PBS and adjusted to a cell density of about $2\sim3\times10^{10}$ cells/liter. Acridine Orange was added to the bovine granulocyte suspension to a final concentration of 50 µg/ml and allowed to stain at ambient temperature for 15 minutes. The granulocytes were isolated by centrifuging at 1200 rpm, washed and re-suspended in PBS. The density of the cells was adjusted to about $2\sim3\times10^{10}$ cells/liter and 1% formaldehyde was added to fix the cells. The fixed granulocytes were isolated by centrifuging at 1200 rpm, washed and re-suspended in PBS, so as to obtain nucleated red blood cell simulating particles.

Figure 9:
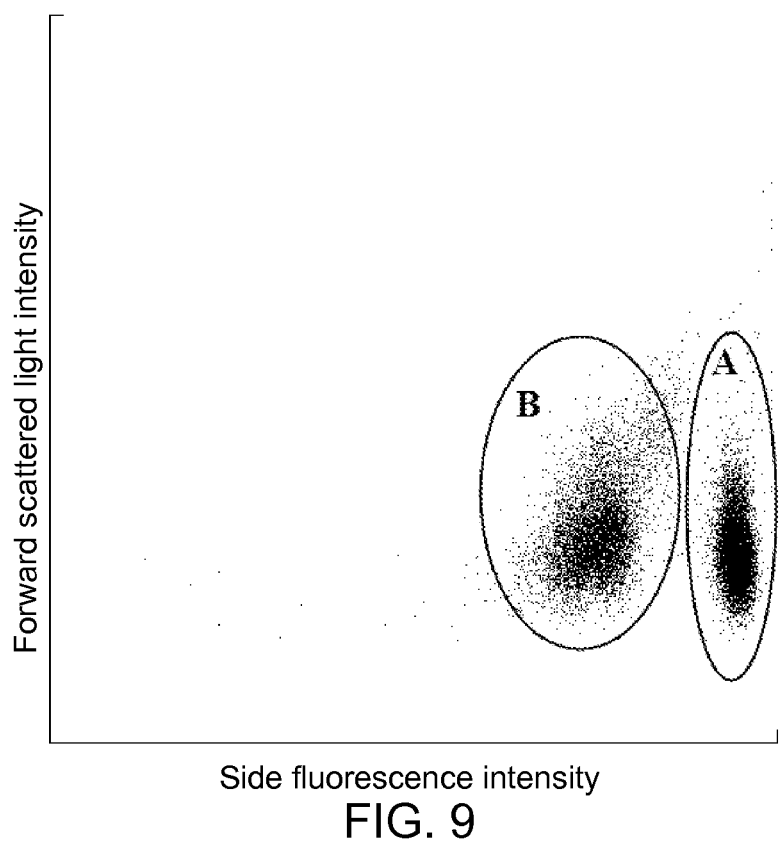
FIG. 9 is a scatter diagram of the mixture of the unstained granulocytes and the granulocytes stained with Acridine Orange in Example 4 (only the channel of the nucleated red blood cells is provided). The abscissa axis represents the side fluorescence intensity, and the longitudinal axis represents the forward scattered light intensity.

A sample of granulocytes fixed by formaldehyde but not stained with Acridine Orange was used as a control sample, were mixed with the nucleated red blood cell simulating particles, and the fixed cells were detected using the reagents and methods as described in above Example 1 to obtain a SFL-FSC scatter diagram as shown in FIG. 9, in which area A is of granulocytes and area B is of nucleated red blood cells.

Example 5

Formulation of a Multi-Component Hematology Control Mixture

Following the protocol shown in Table 1 below, nucleated red blood cell simulating particles prepared according to the present disclosure were mixed with a red blood cell simulator, a platelet simulator and a leukocyte simulator in an appropriate storage solution for formulating multi-component hematology control mixtures with different cell numbers for use in the daily quality control of the BC series flow cytometer with a detection wavelength of 640 nm produced by SHENZHEN MINDRAY BIO-MEDICAL ELECTRONICS CO., LTD.

TABLE 1

| parameter | Low-value hematology control mixture | Middle-value hematology control mixture | High-value hematology control mixture |
|---|---|---|---|
| WBC ($10^9$/L) | 4.0~5.0 | 7.0~8.0 | 18.0~20.0 |
| RBC ($10^{12}$/L) | 2.0~3.0 | 4.0~5.0 | 5.2~5.8 |
| NRBC % | 5%~10% | 5%~10% | 5%~10% |
| PLT ($10^9$/L) | 50~100 | 200~300 | 400~500 |

The use of three hematology control mixtures for the quality control of a hematology analyzer, with a varying number of white blood cells (WBCs), red blood cells (RBCS), nucleated red blood cells (NRBCs), and platelets (PLTs), ensures that the analyzer reports consistent results at the three cell number levels, respectively.

From the above examples, it is shown by the SFL-FSC scatter diagrams that the nucleated red blood cell simulating particles prepared in the Examples of the present disclosure are in the area of nucleated red blood and are distinguishable from leukocytes. They simulate the fluorescent and scattered light properties of the nucleated red blood cells well, and therefore could be useful for the quality control of the classification and counting of nucleated red blood cells.

The data, figures, instruments, reagents and steps herein should be understood to be illustrative, but not restrictive. Although the present disclosure was described with references to the above concrete embodiments, modifications and variances will be apparent to skilled persons in the art. All the modifications and variances fall within the spirit and scope of the disclosure.

The invention claimed is:

1. A multi-component hematology control mixture which contains a nucleated red blood cell simulating particle for analyzing blood samples with a hematology analyzer comprising:
  isolated leukocytes or an isolated leukocyte subpopulation bound to a fluorescent-staining inhibitor, which binds to the nucleus or a nucleic acid in the leukocyte to reduce the binding capacity of the particle to a fluorescent dye used for detection of nucleated red blood cells in the hematology analyzer, wherein the fluorescent-staining inhibitor is selected from at least one of the following:
  a non-fluorescent dye;
  a fluorescent dye with a fluorescence quantum yield lower than that of the fluorescent dye used for detection in the hematology analyzer;
  a fluorescent dye with a fluorescence spectrum which differs from that of the fluorescent dye used for detection in the hematology analyzer in that it is either not excited by or not detected by the hematology analyzer; and
  a compound capable of binding to a nucleoside;
  combined with
    another blood cell simulating agent selected from at least one of simulated red blood cells, simulated leukocytes and simulated platelets, and
    a cell storage solution.

2. The multi-component hematology control mixture of claim 1, wherein the non-fluorescent dye is selected from at least one of the following: Methylene Blue, Toluidine Blue O, Trypan Blue, Safranine T, hematoxylin, Wright's stain and Giemsa stain.

3. The multi-component hematology control mixture of claim 1, wherein the fluorescent dye with a fluorescence quantum yield lower than that of the fluorescent dye used for detection in the hematology analyzer is Neutral Red.

4. The multi-component hematology control mixture of claim 1, wherein the fluorescent dye with a fluorescence spectrum which differs from that of the fluorescent dye used for detection in the hematology analyzer in that it is either not excited by or not detected by the hematology analyzer, is selected from at least one of the following: Acridine Orange, Hoechst 33342, YO-PRO-1 and Propidium Iodide.

5. The multi-component hematology control mixture of claim 1, wherein the compound capable of binding to a nucleoside is Dactinomycin D.

6. The multi-component hematology control mixture of claim 1, wherein the leukocyte subpopulation is granulocytes or lymphocytes.

7. The multi-component hematology control mixture of claim 1, wherein the leukocyte or leukocyte subpopulation is derived from the blood of a mammal or a human.

8. The multi-component hematology control mixture of claim 7, wherein the mammal is selected from at least one of the following: mouse, rat, pig, sheep and cow.

9. A method for preparing the multi-component hematology control mixture of claim 1, comprising:
  enriching the leukocytes or a leukocyte subpopulation in a blood sample comprising leukocytes;
  suspending the obtained leukocytes or leukocyte subpopulation in a cell treatment solution containing a fluorescent-staining inhibitor that stably binds to the nucleus or nucleic acid in a cell, and
  wherein the fluorescent-staining inhibitor is selected from at least one of the following:
    a non-fluorescent dye;
    a fluorescent dye with a fluorescence quantum yield lower than that of a fluorescent dye used for detection in the hematology analyzer;
    a fluorescent dye with a fluorescence spectrum which differs from that of the fluorescent dye used for detection in the hematology analyzer in that it is either not excited by or not detected by the hematology analyzer; and
    a compound capable of binding to a nucleoside;
  washing the obtained product; and
  combining the washed obtained product with
    another blood cell simulating agent selected from at least one of simulated red blood cells, simulated leukocytes and simulated platelets, and
    a cell storage solution.

10. The method of claim 9, wherein the non-fluorescent dye is selected from at least one of the following: Methylene Blue, Toluidine Blue O, Trypan Blue, Safranine T, hematoxylin, Wright's stain and Giemsa stain.

11. The method of claim 9, wherein the fluorescent dye with a fluorescence quantum yield lower than that of the fluorescent dye used for detection in the hematology analyzer is Neutral Red.

12. The method of claim 9, wherein the fluorescent dye with a fluorescence spectrum which differs from that of the fluorescent dye used for detection in the hematology analyzer in that it is either not excited by or not detected by the hematology analyzer, is selected from at least one of the following: Acridine Orange, Hoechst 33342, YO-PRO-1 and Propidium Iodide.

13. The method of claim 9, wherein the compound capable of binding to a nucleoside is Dactinomycin D.

14. The method of claim 9, wherein the leukocyte subpopulation is granulocytes or lymphocytes.

15. The method of claim 9, wherein the leukocyte or leukocyte subpopulation is derived from the blood of a mammal or a human.

16. The method of claim 15, wherein the mammal is selected from at least one of the following: mouse, rat, pig, sheep and cow.

17. The method of claim 9, further comprising the step of fixing the leukocytes or leukocyte subpopulation, and/or storing the leukocytes or leukocyte subpopulation.

18. A method of using a multi-component hematology control mixture for the detection of nucleated red blood cells, comprising:
   providing the multi-component hematology control mixture of claim 1 to a hematology analyzer, and
   analyzing the multi-component hematology control mixture in the hematology analyzer.

* * * * *